(12) United States Patent
Puleo et al.

(10) Patent No.: US 9,999,856 B2
(45) Date of Patent: Jun. 19, 2018

(54) METHODS FOR ELECTROELUTION OF BIOMOLECULES

(71) Applicant: General Electric Company, Schenectady, NY (US)

(72) Inventors: Christopher Michael Puleo, Niskayuna, NY (US); John Richard Nelson, Clifton Park, NY (US); Patrick McCoy Spooner, Slingerlands, NY (US); Ralf Lenigk, Niskayuna, NY (US); Nichole Lea Wood, Niskayuna, NY (US); Li Zhu, Clifton Park, NY (US); Craig Patrick Galligan, Niskayuna, NY (US)

(73) Assignee: General Electric Company, Schenectady ( * ) Notice: Subject to any disclaimer, the term of this patent is extended or adjusted under 35 U.S.C. 154(b) by 86 days.

(21) Appl. No.: 13/951,881

(22) Filed: Jul. 26, 2013

(65) Prior Publication Data
US 2015/0027891 A1    Jan. 29, 2015

(51) Int. Cl.
*B01D 57/02* (2006.01)
*C12N 15/10* (2006.01)

(52) U.S. Cl.
CPC ......... *B01D 57/02* (2013.01); *C12N 15/101* (2013.01)

(58) Field of Classification Search
CPC ...... C12Q 1/6806; C12Q 1/68; C12Q 1/6802; G01N 27/447; G01N 27/44704; G01N 27/44756; G01N 27/44769; G01N 27/44791

USPC ......................................................... 435/6.1
See application file for complete search history.

(56) References Cited

U.S. PATENT DOCUMENTS

| | | | |
|---|---|---|---|
| 4,750,982 A | 6/1988 | Tomblin et al. | |
| 5,028,308 A | 7/1991 | Beritashvili et al. | |
| 5,730,850 A | 3/1998 | Kambara et al. | |
| 6,129,828 A * | 10/2000 | Sheldon, III | B01D 57/02 204/465 |
| 6,168,922 B1 * | 1/2001 | Harvey | C12N 15/1003 435/2 |
| 6,255,050 B1 * | 7/2001 | Nie et al. | 435/6.12 |
| 6,929,730 B2 | 8/2005 | Lee et al. | |
| 6,984,516 B2 | 1/2006 | Briscoe et al. | |
| 8,034,225 B2 | 10/2011 | Riveron Rojas et al. | |

(Continued)

OTHER PUBLICATIONS

Lee et al, "Reversible Capture of Genomic DNA by a Nafion-Coated Electrode," Analytical Biochemistry 380 (2008) 335-337.*

(Continued)

*Primary Examiner* — Luan V Van
*Assistant Examiner* — Salil Jain
(74) *Attorney, Agent, or Firm* — GE Global Patent Operation; John Darling

(57) ABSTRACT

A method of eluting biomolecules, such as nucleic acids from a biological sample by electroelution is provided. An example of a method includes various steps, such as loading the biological sample to a device comprising a housing, at least two conductive redox polymer electrodes operationally coupled to the housing and a biomolecule impermeable layer disposed on at least one of the electrodes. The loading of sample is followed by initiating an electrical connection to generate an electric field strength sufficient to elute biomolecules from the biological sample; and eluting the biomolecules from the biological sample.

20 Claims, 8 Drawing Sheets

(56) References Cited

U.S. PATENT DOCUMENTS

| | | | |
|---|---|---|---|
| 8,062,846 B2 | 11/2011 | Bortolin et al. | |
| 2002/0121444 A1* | 9/2002 | Lee et al. | 204/613 |
| 2003/0133846 A1* | 7/2003 | Ben-Asouli et al. | 422/102 |
| 2004/0050700 A1 | 3/2004 | Lopez-Canovas et al. | |
| 2004/0069635 A1* | 4/2004 | Mitsuhashi et al. | 204/456 |
| 2008/0108119 A1 | 5/2008 | Jensen et al. | |
| 2009/0178923 A1* | 7/2009 | Marquant et al. | 204/403.01 |
| 2009/0294307 A1* | 12/2009 | Liu et al. | 205/792 |
| 2011/0105997 A1 | 5/2011 | Berggren et al. | |
| 2011/0244467 A1* | 10/2011 | Haswell | 435/6.12 |
| 2012/0152743 A1 | 6/2012 | Finehout et al. | |
| 2012/0312384 A1 | 12/2012 | Robinson et al. | |
| 2013/0153425 A1* | 6/2013 | Puleo et al. | 204/627 |
| 2013/0156615 A1* | 6/2013 | Puleo et al. | 417/410.1 |

OTHER PUBLICATIONS

International Search Report and the Written Opinion of the International Searching Authority issued in connection with corresponding WIPO Application PCT/EP2014/066098 dated Feb. 19, 2015.

Evans, John, "Electrodes get reactive: Electrophoresis without unwanted chemical reactions," XP002735618, Apr. 10, 2011.

Erlandsson, Per, G, et al., "Electrolysis-reducing electrodes for electrokinetic devices," Electrophoresis, vol. 32, No. 6-7, Mar. 2011 pp. 784-790.

Zarzosa-Alvarez, et al., "Electroeluting DNA Fragments," XP002735620, Sep. 5, 2010.

\* cited by examiner

METHODS FOR ELECTROELUTION OF BIOMOLECULES

SEQUENCE LISTING

The instant application contains a Sequence Listing which has been submitted in ASCII format via EFS-Web and is hereby incorporated by reference in its entirety. Said ASCII copy, created on Jun. 26, 2013, is named 270553-1_SL.txt and is 1,238 bytes in size.

FIELD

The invention relates to methods for eluting biomolecules from a biological sample. The invention further relates to a device and a system for elution of nucleic acids and associated methods for eluting nucleic acids from a biological sample by electroelution.

BACKGROUND

Preparation and manipulation of high quality nucleic acids are primary requirements for a variety of applications, such as analyte-detection, sensing, forensic and diagnostic applications, genome sequencing, and the like. Electrophoretic manipulation of biomolecules such as nucleic acids is a mainstay in molecular and cell biology. Electrophoretic manipulation comprises gel electrophoresis, capillary electrophoresis, and electrophoresis in microfluidic or microanalytical devices, which enable purification and separation of specific biomolecules.

An electrophoresis setup generally uses standard metal electrodes, wherein the gases produced as by-products during electrode side-reactions may affect the chemical composition or pH of the liquid buffer, especially for a buffer volume with a comparatively lower buffer capacity. Therefore, challenges are associated with the use of standard metal electrodes in miniaturized devices, where the by-products generated in the presence of standard metal electrodes may destroy the utility of these small devices. This is due to the limited volume of liquid buffer available in the small devices and their inability to prevent the effect of the by-products, such as effect of a gas on the chemical composition or pH of the liquid buffer.

Redox polymer electrodes remain an intriguing alternative to metal electrodes in bio-analytical systems due to their ability to perform electron-to-ion transduction across redox electrode-liquid interfaces and reduce detrimental electrode side reactions. The redox polymer electrodes have become popular due to their excellent charge transfer properties, ease of implementing the liquid precursors into standard high-volume manufacturing processes and relatively lower production costs. However, the effects of the redox polymer electrodes on nucleic acids have not been reported so far.

For nucleic acid purification devices, biologically inert electrode material is desired. Single-use disposables, which may reduce or eliminate set-up and hands-on time during operation, remains one of the objectives. Therefore, there is a substantial need for smaller, simpler, inexpensive devices for faster elution of nucleic acids. A method for purification and elution of nucleic acids from a biological sample with minimal human intervention and in less time is therefore desirable.

BRIEF DESCRIPTION

An example of a method of eluting biomolecules from a biological sample, comprises loading the biological sample to a device comprising a housing, at least two conductive redox polymer electrodes operationally coupled to the housing and a biomolecule impermeable layer disposed on at least one of the electrodes; initiating an electrical connection to generate an electric field strength sufficient to elute biomolecules from the biological sample; and eluting the biomolecules from the biological sample.

In another example, a method of eluting biomolecules from a biological sample, comprises loading a biological sample laden substrate to a housing of a device comprising the housing, at least two conductive redox polymer electrodes operationally coupled to the housing and a biomolecule impermeable layer disposed on at least one of the electrodes; initiating an electrical connection to generate an electric field strength sufficient to elute biomolecules from the biological sample; and eluting the biomolecules from the biological sample.

DRAWINGS

These and other features, aspects, and advantages of the present invention will become better understood when the following detailed description is read with reference to the accompanying drawings in which like characters represent like parts throughout the drawings, wherein.

FIG. 4 A is an image of a DNA gel electrophoresis of an electroeluted DNA with (+) and without (−) treatment with a DNA degradation agent. FIG. 4 B is an image of DNA gel electrophoresis following a PCR amplification of the nucleic acids shown in FIG. 4 A.

Figure 5:
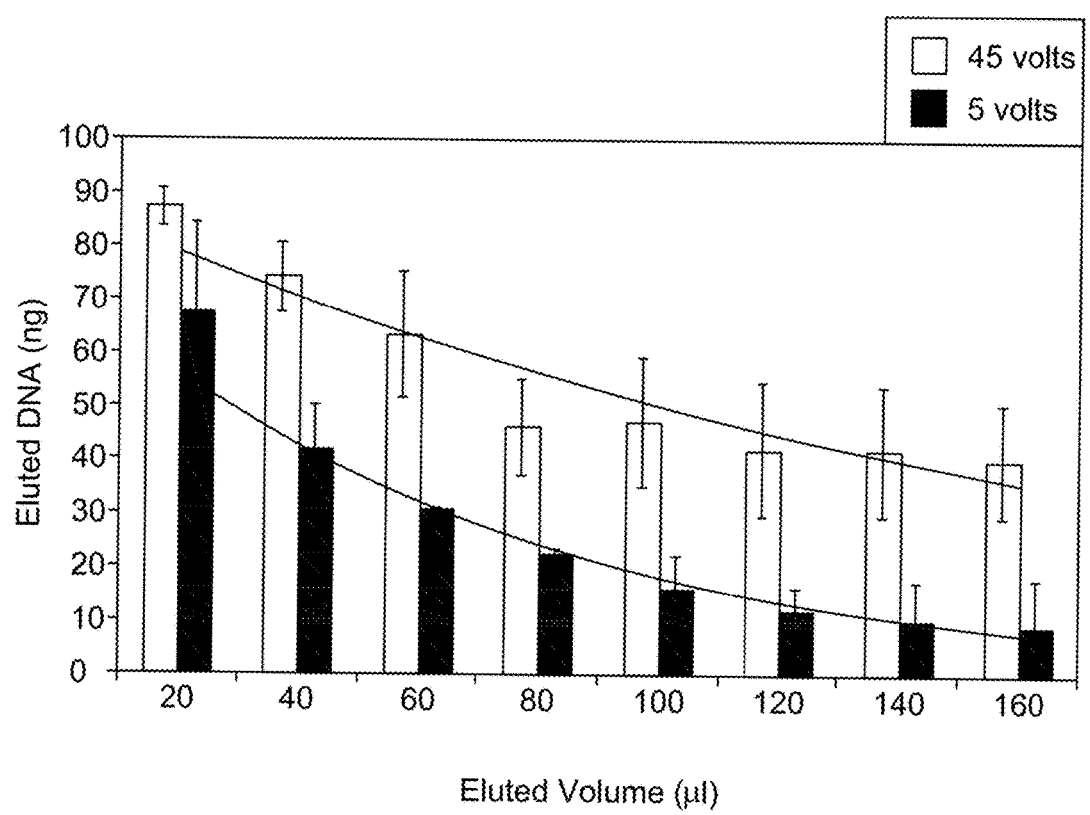

FIG. 5 is a graph showing an elution profile of DNA from FTA® paper using different applied voltage.

Figure 6:
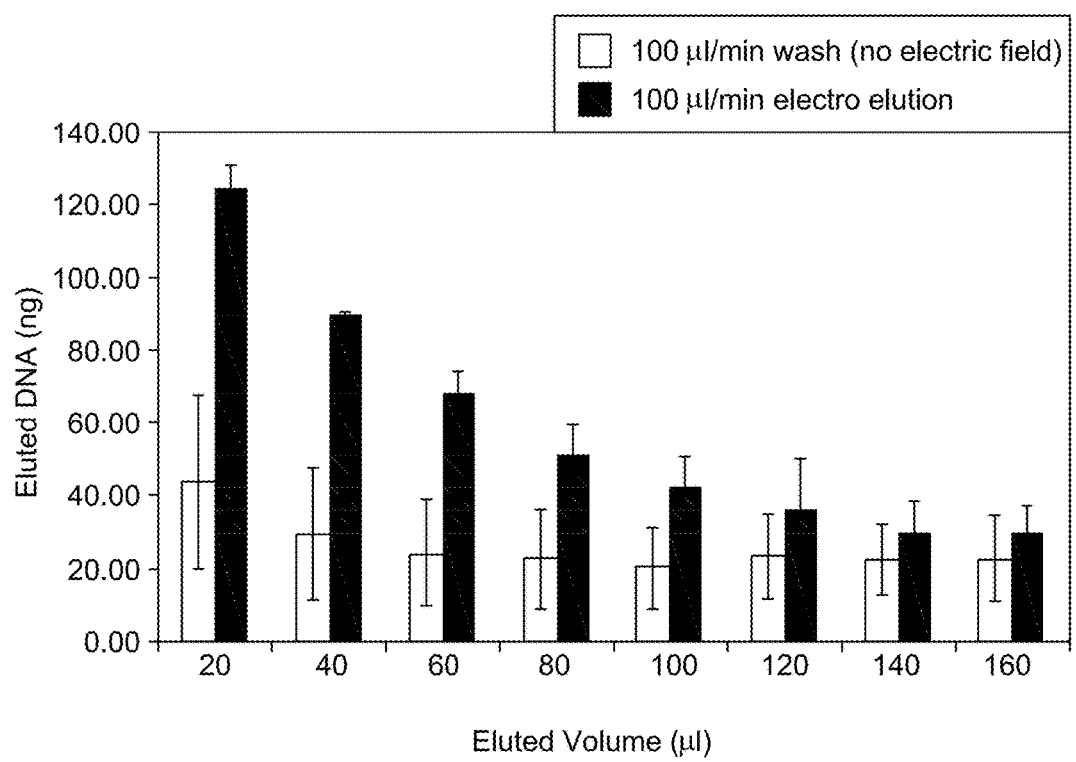

FIG. 6 is a graph showing an elution profile of lambda DNA at an applied voltage of 25 V and an elution of DNA using wash buffer with no applied electric field.

Figure 7:
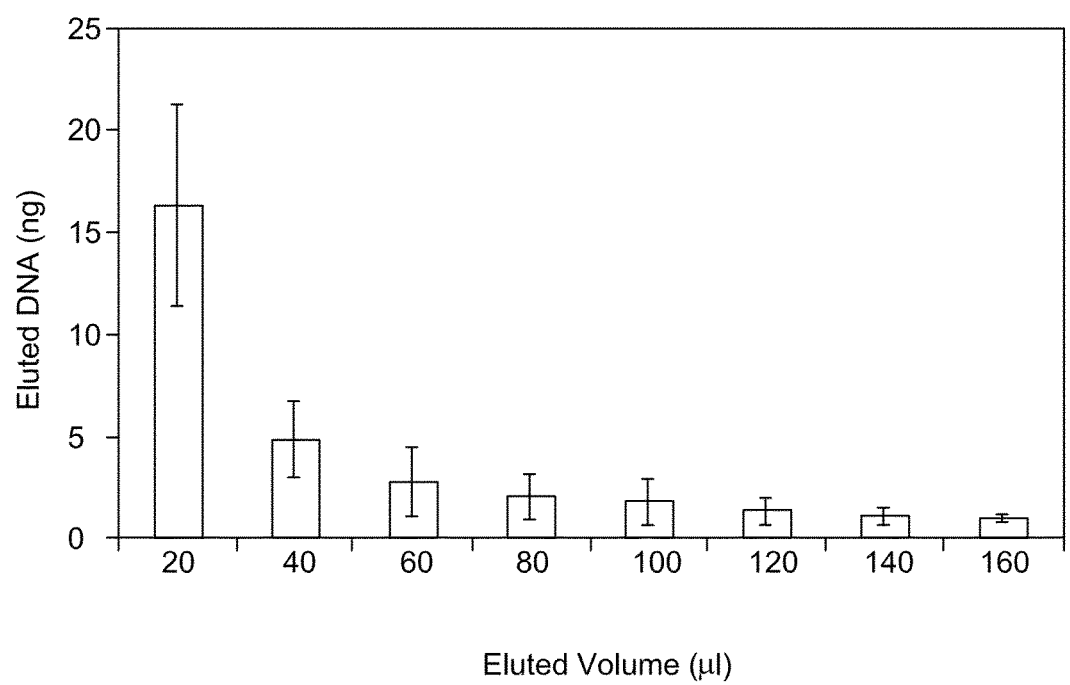

FIG. 7 is a graph showing an elution profile of a real field sample of DNA eluted directly from a buccal cell collector at an applied voltage of 25 V for 5 minutes.

Figure 8:
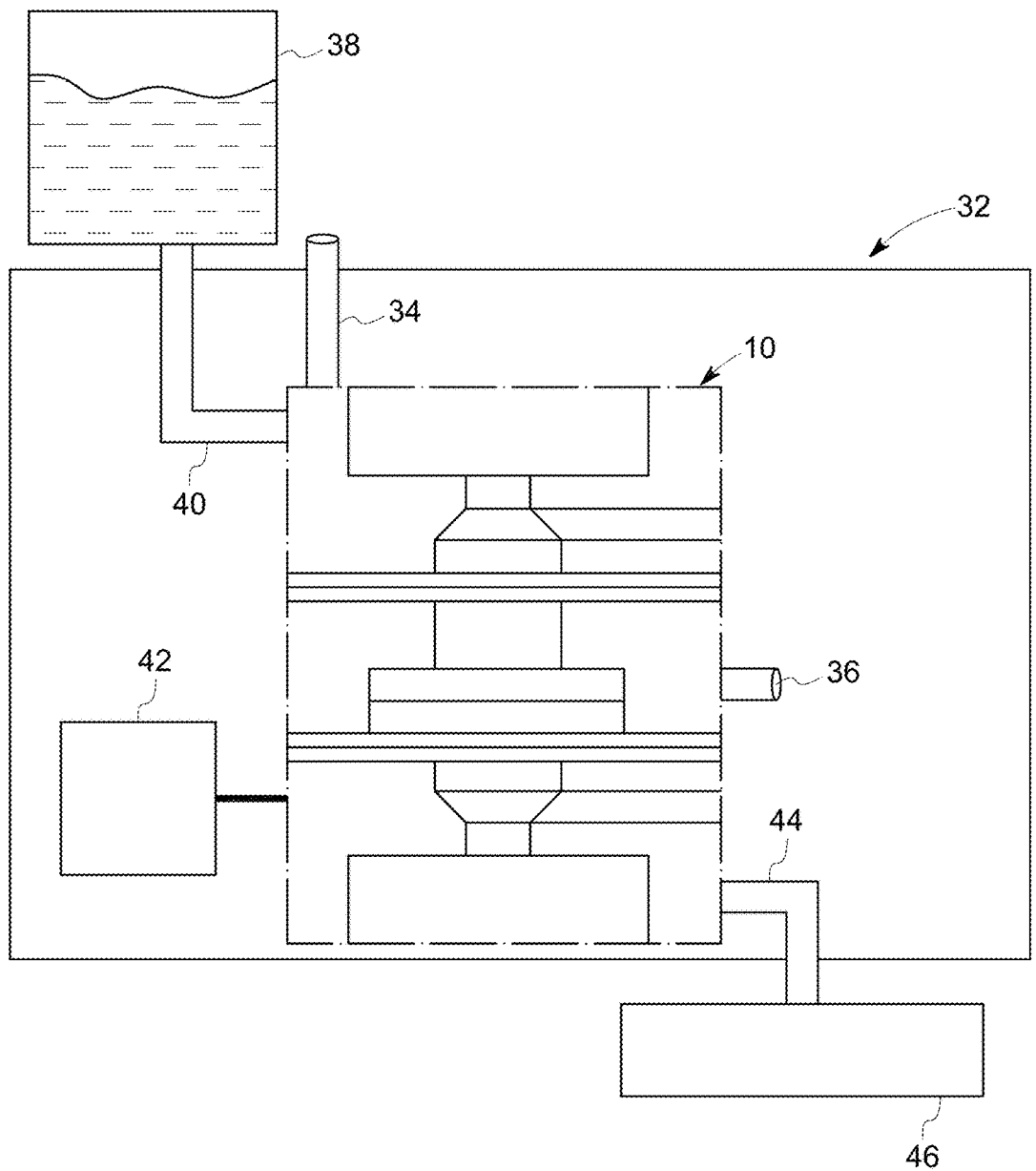

FIG. 8 is a schematic drawing of an example of one embodiment of a system of the invention.

DETAILED DESCRIPTION

The invention provides methods for isolating and eluting biomolecules, such as nucleic acids, from a wide variety of samples, including for example, bacteria, plants, blood or buccal swabs, with a greater simplification using an elution device. Embodiments of the method comprises loading a sample or a sample laden substrate to an elution device comprising a housing, at least two conductive redox polymers electrodes operationally coupled to the housing, and eluting high quality biomolecules, such as nucleic acids from the sample.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, the term "operatively coupled" or "operationally coupled" refers to a functional interaction between one or more components during operation, such as electroelution. For example, electrodes are operationally coupled to the housing of the device during electroelution.

As used herein, the term "biomolecule impermeable layer" refers to a layer or membrane or coating that is impermeable to biomolecules, such as nucleic acids, however the layer is permeable to ions. The layer may be formed by disposing a solid, semi-solid or liquid material on the electrodes which render the layer permeable to ions and impermeable to biomolecules, such as nucleic acids. The biomolecule impermeable layer may also include a "coating". The coating may be deposited on the electrodes to prevent direct contact of biomolecules and the electrodes. For example, the coating forms a barrier between the nucleic acids, such as DNA and the electrode materials, such as poly(3,4-ethylenedioxythiophene) poly(styrenesulfonate) or Pedot:PSS.

As used herein, the term "conductive redox polymers" refers to polymers, which contain functional groups that can be reversibly reduced or oxidized. These spatially localized redox sites render the polymer conductive through electron exchange between neighboring sites, and may either be covalently attached to the polymer chain or electrostatically attached. The polymers are electrochemically active, and may be used for "electron-to-ion" transport across an electrode-electrolyte interface in order to preserve charge neutrality within an electrochemical cell.

As used herein, the term "components of the electrode materials" refers to the constituents of the electrode materials comprising one or more monomers or polymers. The components may include electrode-degradation materials which may release on the degradation of the electrodes, for example, during electroelution. The component may be, for example, poly(3,4-ethylenedioxythiophene) or Pedot.

An embodiment of a method of eluting biomolecules from a biological sample, comprises loading the biological sample to a housing of a device wherein the device comprises the housing, at least two conductive redox polymer electrodes operationally coupled to the housing and a biomolecule impermeable layer disposed on at least one of the electrodes. The loading of sample is followed by initiating the device with an electrical connection to generate electric field strength sufficient to elute biomolecules from the biological sample; and eluting the biomolecules from the biological sample.

Figure 1:
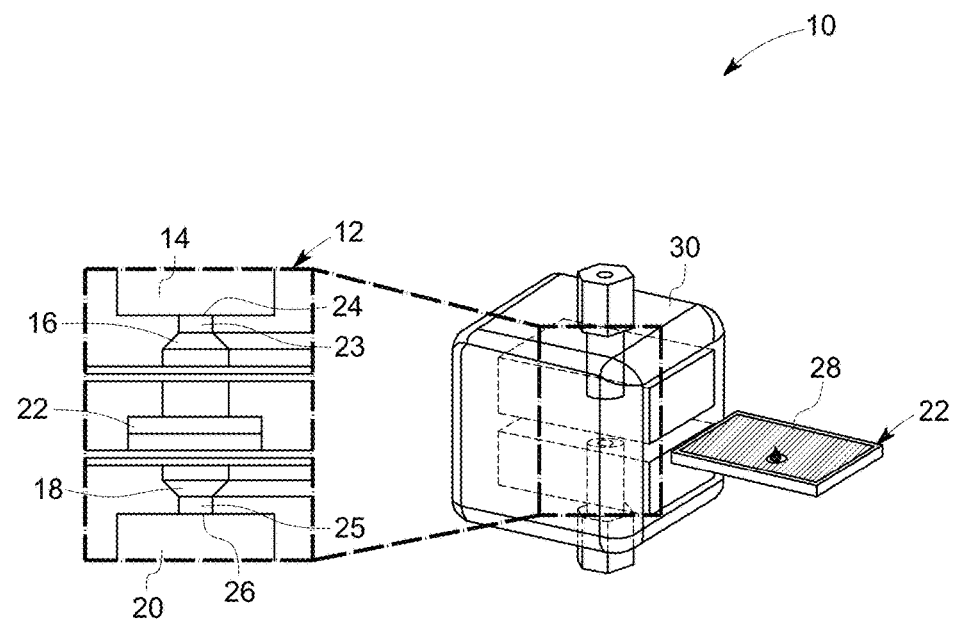
FIG. 1 is a schematic drawing of an example of an embodiment of a device of the invention.
Figure 2:
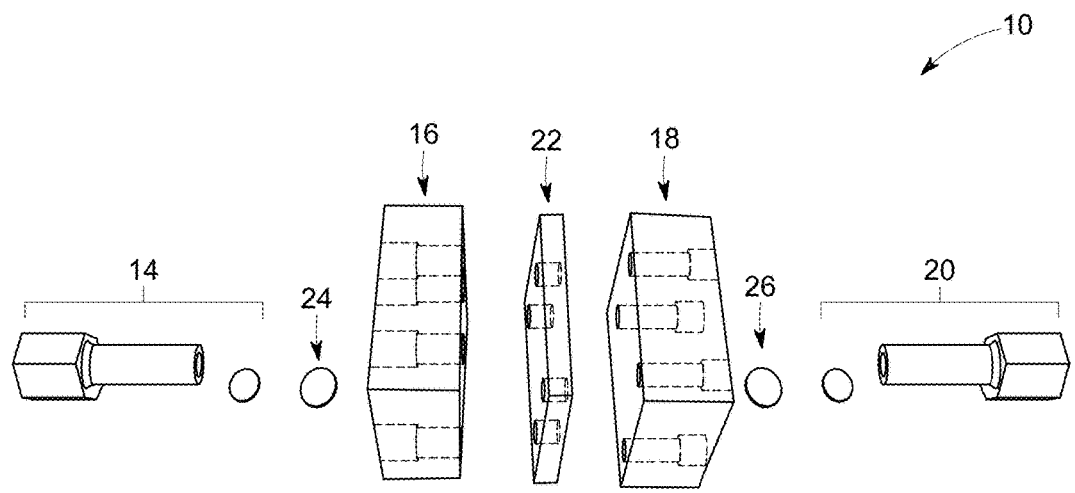
FIG. 2 is an image of an example of a disassembled embodiment of a device of the invention.

In one or more examples of methods, the biomolecules are eluted from a sample using an elution device, wherein the device comprises a housing configured to receive an electrolyte and the biological sample comprising biomolecules, at least two electrodes comprising conductive redox polymers operationally coupled to the housing, and a biomolecule impermeable layer disposed on at least one of the electrodes to prevent contact between the conductive redox polymers and the biomolecules. Non-limiting examples of an embodiment of the device are shown in FIGS. 1 and 2. The term "biological sample" is interchangeably used herein with "biological material". In some other embodiments, a device for elution of biomolecules from a biological sample, comprises a housing configured to receive a biological sample laden substrate and at least two electrodes comprising cross-linked conductive redox polymers, wherein the substrate and the electrodes are operationally coupled to each other. The housing may include a chamber, a cartridge, a channel or a container. In some embodiments, the housing comprises a microfluidic channel. The housing may be an hermetically sealed liquid filled chamber, a reservoir or a microfluidic channel. Some embodiments of the housing may further comprise one or more chambers configured to receive liquids, such as wash buffer or elution buffer. The housing is described in greater detail with reference to FIGS. 1 and 2 hereinafter.

The loading of the biological sample may be achieved by direct loading of the biological sample to the housing, loading of a biological sample laden substrate to the housing, loading of the biological sample in a package configured to release the sample during operation or combinations thereof. In the case of loading a sample laden substrate, such as a forensic sample may be collected from a field, dried on the substrate and loaded to the device before electroelution. In some examples, the sample is loaded to a FTA®-cellulose substrate or a FTA® card, dried and may be store for few days before subject to electroelution of the biomolecules from the sample. As noted, in this embodiment, the substrate may comprise one or more cell-lysis reagents. In some embodiments, the method further comprises hydrating the cell lysis reagent on the substrate to extract the biomolecules from the biological material. In some examples, the loading may be a direct loading to the housing, wherein no substrate is inserted to the device for loading the sample. In some other embodiments, the sample is loaded to the substrate and inserted to the device before electroelution.

In some embodiments, the electrolyte is added to provide a conduction path for electron-ion transfer. In some embodiments, the dried buffer reagents may be stored in the housing or placed on a substrate, which may be reconstituted to an electrolytic solution or a buffer solution on addition of water or buffer to the housing. In some embodiments, the method further comprises wetting the electrodes, by loading an electrolyte to the housing. The electrolyte is also loaded to wet the biomolecule impermeable layer.

The method further comprises electrophoretically eluting the biomolecules from the biological sample. Generally the external electrical contacts are provided to the device with either crimped metal, conductive adhesives, or direct contact to the electrode, such as PEDOT:PSS electrode layer to initiate the electrochemical reaction.

In some embodiments, the device is devoid of a substrate, wherein the sample is directly loaded to the housing. In these embodiments, the electrodes are in contact with the sample comprising biomolecules, such as nucleic acids. The electrodes provide an electrophoretic force for eluting the nucleic acids from the biological sample loaded into the housing.

In some embodiments, the nucleic acids are eluted from a biological sample wherein the sample is applied on the substrate. In these embodiments, the sample laden substrate is pre-loaded to the housing. In the embodiments, wherein the sample laden substrate is pre-loaded, the electrodes are in contact with the substrate. The electrodes provide an electrophoretic force for eluting the nucleic acids from the biological sample disposed on the substrate which is in contact with the electrodes. In some other embodiments, the electrodes are placed near the substrate and provide an electrophoretic force for eluting the nucleic acids from the biological sample disposed on the substrate.

The method further comprises electrophoretically driving the eluted biomolecules from the sample to the surface of the electrodes. The biomolecules are captured on the coated electrode surface, wherein the electrodes are coated with the biomolecule impermeable layer. The biomolecules, for example nucleic acids are captured on the biomolecule impermeable layer present on the electrode.

The method further comprises eluting out the impurities from the housing. The term "impurities" is referred to herein as the materials eluted out from the sample, which does not contain the biomolecules of interest, such as nucleic acids. For example, the nucleic acids are captured on the surface of the coated electrodes, wherein the coating is of biomolecule impermeable layer. The liquid, such as an electrolyte or a buffer, present in the device (housing) comprises any material other than the nucleic acids of interest eluted from the sample may be considered as impurities. These impurities may be eluted out from the device before elution of the nucleic acids which are captured to the biomolecule impermeable layer.

In some embodiments, the method further comprises releasing the biomolecules from the surface of the electrodes. In these embodiments, the biomolecules are released from the biomolecule impermeable layer. The biomolecule impermeable layer may include a regenerated cellulose or Nafion®. The biomolecules may be eluted from the biomolecule impermeable layer by reversing an ion-conduction between the electrodes. In one or more embodiments, a negative voltage is applied to the biomolecule impermeable layer disposed on the electrodes, wherein the nucleic acids of interest are bound thereto. The nucleic acids bound to the biomolecule impermeable layer are eluted by using a negative voltage, wherein the negative voltage acts as an electrostatic repulsion to the negatively charged nucleic acids. The bound nucleic acids are detached from the regenerated cellulose layer due to charge repulsion. The nucleic acids may be partially entangled to the biomolecule impermeable layer, or the ends of the nucleic acids may be inserted into the pores of the biomolecule impermeable layer. In absence of driving charge, the nucleic acids may fall off from the biomolecule impermeable layer.

One or more examples of the method further comprise eluting the released nucleic acids from the housing and collecting outside of the device for further application. For eluting the nucleic acids from the device require about 50 V/cm of field strength. In one or more embodiments, field strength of 50 V/cm to 200 V/cm is applied to elute the nucleic acids from the device. The eluted nucleic acids may be collected to a container and stored for future use.

Electric field strength of at least 25 V/cm is generated for electroelution of the biomolecules. The field strength may be in a range of about 25 V/cm to 200 V/cm. In some embodiments, the electrode formulation and structure enabled developing field strength of above 100 V/cm. In these embodiments, the field strength of above 100 V/cm may be achieved by a small disposable/battery operated package. The electric field strength of 5V/cm, 25V/cm and 45V/cm were used for elution of nucleic acids from the substrate, such as FTA® as shown in FIG. 5. The electric field strength of 25V/cm applied across FTA® substrate is sufficient for efficient elution of embedded lambda DNA in less than 1 minute, as shown in FIG. 6. For eluting the released nucleic acids from the housing, the electric field strength of at least about 50 V/cm may be sufficient.

In some other embodiments, the method further comprises washing the biomolecule impermeable layer after capturing the nucleic acids with the wash buffer; followed by eluting the nucleic acids from the layer using an elution buffer.

As noted, the method employs a device for electroelution, wherein FIG. 1 illustrates a schematic drawing of a non-limiting example of an overall device structure 10, and the inset is magnified to show various parts of the device. In FIG. 1, the magnified image shows the housing 12 comprising various components of the device 10. The device 10 comprises a conducting polymer electrode 14 and an inlet and cathode chamber 16 as part of the first component. A conducting polymer electrode 20 and an outlet and anode chamber 18 constitute the second component. In some exemplary embodiments, the inlet and the outlet are associated with one or more chambers, wherein the inlet or cathode chamber 14 and the outlet or anode chamber 18 may comprise elution buffer. The device may further comprise a substrate holder or a cartridge 22 as a third component, wherein the substrate holder or cartridge comprises the substrate 28, e.g., a cartridge comprising FTA™. A biomolecule impermeable layer 24 is disposed on to the oxidizing electrode 14, and a biomolecules impermeable membrane 26 is disposed on to the reducing electrode 20. In some embodiments, the third component, such as substrate holder or cartridge 22 comprising substrate 28, may be inserted into the device 10 during operation. The operation in this example is electroelution of nucleic acids from a biological sample. In one or more exemplary embodiments, the cartridge 22 comprising substrate 28 is inserted between the two components, the first component and the second component, as an intervening layer or component, as illustrated in FIG. 1, device 10. In some embodiments, the device comprises a first component and a second component, wherein the device is devoid of a separate third component or the substrate. In these embodiments, the sample is loaded from outside to the housing 12.

Another non-limiting embodiment of the device 10 is illustrated by an image of FIG. 2, wherein various components of the device are shown, in order, before assembly to constitute the device 10. The components, as shown in FIG. 2 include oxidizing electrode 14, biomolecule impermeable layer 24 for disposing on to the oxidizing electrode 14, inlet cathode chamber 16, substrate cartridge 22, outlet anode chamber 18, biomolecules impermeable membrane 26 for disposing on to the reducing electrode 20. The substrate may be encased in or disposed on or embedded in a cartridge 22. In some embodiments, as mentioned, a sample may be loaded on the substrate 28 within the cartridge 22, wherein the substrate 28 is placed outside of the device. The sample laden substrate 28 is then inserted into the device during elution of the biomolecules from the sample. In some other embodiments, the sample is directly loaded to the housing, in presence or absence of a substrate 28. In some embodiments, the components are packaged separately, and can be assembled with device 10 before use for electroelution. In some exemplary embodiments, an elution buffer or an electrolyte is present in the housing 12 during electroelution.

One example of method for isolating nucleic acids comprises various steps including sample loading, washing, or eluting the nucleic acids. During operation, the biological sample is loaded onto the substrate 28. The substrate is impregnated with or without cell lysis reagents. In one exemplary embodiment, the substrate may comprise cell lysis reagents or nucleic acid stabilizing reagents. The sample is loaded to the substrate and air is introduced to the substrate for drying the sample, in some embodiments, the sample is rapidly dried using a fan or a heater. In some embodiments, the sample laden substrate is inserted into the device for isolating nucleic acids from the substrate 28. The sample loading is followed by initiating the current flow through the electrolyte and across the substrate. The nucleic acids from the sample are electroeluted and driven towards the electrodes coated with biomolecule impermeable layer. The nucleic acids are deposited on the biomolecule impermeable layer, whereas the ions can pass through the layer. In an exemplary embodiment, the electrodes are washed with washing buffer to elute out the undesired materials of the sample. Finally, the nucleic acids deposited on the coated surface of the electrodes are electroeluted by reversing the current flow and is collected outside the device for downstream applications.

As noted, one or more embodiments of the method employ conductive redox polymer electrodes. In some embodiments, conductive polymers may be selected from polyacetylenes, polyphenylene vinylenes, polypyrroles, polythiophenes, polyanilines, polyphenylene sulfide or polyfluorenes. In some embodiments, the electrodes are made of a base material, such as a macroporous polymer, coated with a conductive material. In one embodiment, the electrodes are coated with redox polymer, redox metal salts or metal oxides. In some embodiments, the electrodes are coated with redox polymers, which include but are not limited to PEDOT, PEDOT:PSS, Poly(1,5-diaminoanthraquinone), poly(2-2-dithiodianiline) or pDTDA. The electrode may be coated with a conductive or redox polymer on a thick porous substrate.

In some embodiments, the conductive redox polymer comprises a Pedot: PSS material. In some embodiments, the device utilizes cellulose as a substrate to increase the surface area of the redox polymer electrode, and thus the redox capacity. The Pedot: PSS electrodes enable electron-ion conduction in an electroelution device without generating a by-product such as a gas which may affect the elution process, especially when the device is a small microfluidic or micro-analytical device. In the absence of sufficient venting, which adds considerable technical challenges, air bubbles generated during the process may reduce conductivity and prevent any subsequent fluidic manipulations. The Pedot:PSS establishes higher electric field strength across the channel for electroelution without forming a gas as an undesired by product. In one embodiment, the electrode comprises conductive redox polymers of 0.05 µg-0.5 mg per mm² of electrode surface and the electrodes are coupled to the housing. In some embodiments, the electrodes are configured to generate electric field strength of at least about 25 V/cm. In some embodiments, the electrodes are configured to generate an electric field strength of at least about 400 V/cm.

The use of standard conductive electrode materials, such as conductive monomers or polymers for electroelution of the biomolecules may have an effect on downstream biological applications. The effect of standard conductive monomers or polymers including PSS monomers, PSS polymers and Pedot: PSS polymers on amplification of nucleic acids by polymerase chain reaction (PCR) was determined and the data is presented in Table 1. The conductive redox polymer electrode materials were added into the PCR mixture at different concentrations and the threshold of inhibition was measured at $6.5 \times 10^{-5}$ ppm for Pedot: PSS and PSS polymer and at 0.65 ppm for the PSS monomer. Successful amplifications are denoted with a "+", successful but delayed (higher than expected $C_t$ value) amplifications are denoted with "+/−", while completely inhibited reactions are denoted with a "−".

The result of the inhibition assay as presented in Table 1 shows that the standard electrode materials have a deleterious effect on nucleic acid amplification. Pedot:PSS polymer inhibits the amplification reaction even when present in a very low concentration, $6.5 \times 10^{-5}$ ppm. During electroelution, the discharge of electrode materials may cause detrimental effects on nucleic acids and the downstream applications, such as amplification of the nucleic acids. The electrode materials may be modified or treated to eliminate or reduce the probability of discharge of electrode-degradation materials during electroelution.

In one or more embodiments, the electrode materials are subjected to various treatments to prevent discharge of the electrode-materials during the elution process. The treatment may include cross-linking of the polymers. In one or more embodiments, the electrode materials are conductive redox polymers, wherein the conductive redox polymers are cross-linked to prevent leaching of one or more electrode-degradation materials from the electrodes. In some embodiments, the cross-linking includes ionic cross-linking. For example, $Mg^{+2}$ ions are used as ionic cross-linkers for cross-linking of the Pedot:PSS polymer. In an exemplary embodiment, the Pedot:PSS cellulose electrodes are soaked in 0.25 M $MgSO_4$ to provide ionic cross-linking of Pedot:PSS polymers within the cellulose matrix. In some embodiments, the conductive redox polymers may be modified by cross-linking two or more of the modified polymers, such as amine, or photoactive cross-linkers may be used to cross-link the polymers. For example, a photoactive cross-linker, methacrylate is used to form methacrylate modified PEDOT. In some other embodiments, the conductive redox polymers may be modified by cross-linking the polymers or dopant. In some other embodiments, the conductive redox polymers may be modified by cross-linking two or more of the polymers or polymers and dopant or both. The dopants may include but is not limited to PSS, ZnO, sorbitol, polyethylene glycol or PEG.

Figure 3:
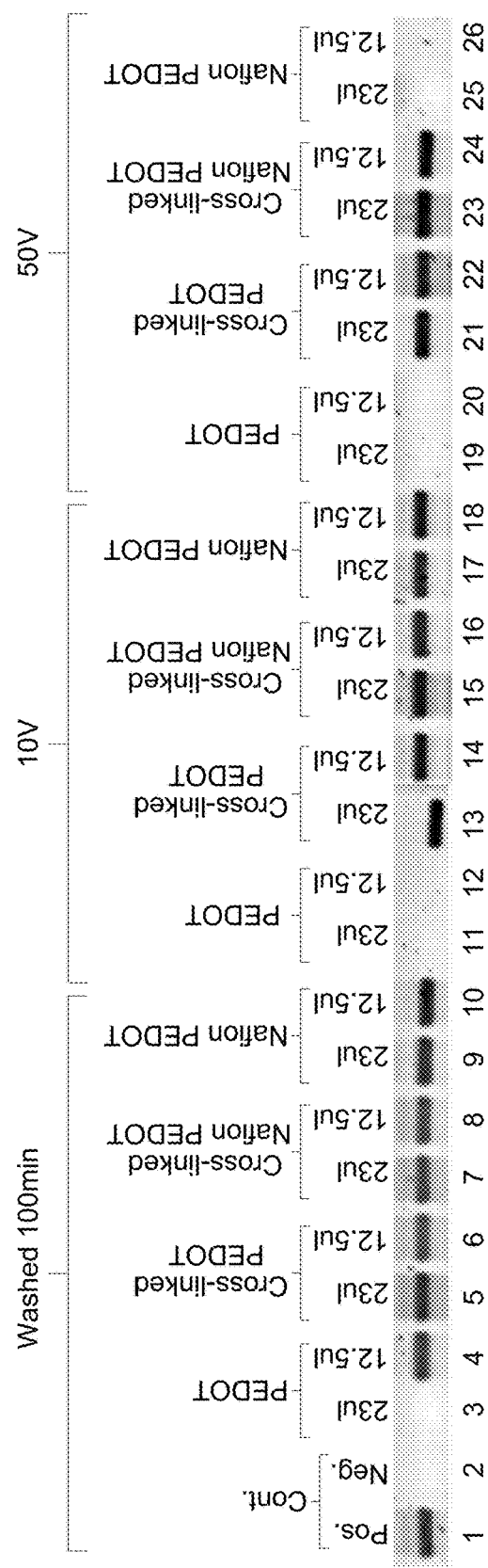
FIG. 3 is an image of a DNA gel electrophoresis of a PCR amplification product, wherein the template nucleic acids were recovered by electroelution in the presence of different redox polymer electrodes.

The effect of treated and un-treated Pedot:PSS material as high capacity electrodes in microfluidic devices on downstream applications, such as nucleic acid amplification, was determined FIG. 3 (image of DNA gel electrophoresis) clearly shows the effect of treated or un-treated Pedot:PSS electrode material on nucleic acid amplification. The PCR inhibition is prevented when the Pedot:PSS electrodes are cross-linked at 0V, 10V and 50V respectively (lanes 5-6; 13-14 and 21-22). The cross-linking of the electrode materials prevents leaching of the electrode-degradation materials during electroelution, which results in PCR amplification reactions without inhibition.

As noted, in some embodiments, the biomolecule impermeable layer is disposed on the electrodes to prevent contact between the conductive redox polymers and the biomolecules. In this embodiment, the biomolecule impermeable layer creates a barrier between the collected biomolecules and the redox electrode, which may further prevent damage to the eluted nucleic acids. The use of biomolecule impermeable layer is to avoid contact between the biomolecules and the redox active electrodes. The biomolecules, such as nucleic acids, may be eluted from the sample and driven towards the electrode, wherein the interaction between uncoated-electrode and nucleic acids, like DNA, results in DNA damage or degradation. In some embodiments, the DNA may have oxidative damages if contacted with the redox active electrodes. The damage of nucleic acids may be reduced or prevented using the biomolecule impermeable layer which prevents contact between the nucleic acid and the conductive electrode. In some embodiments the biomolecule impermeable layer captures the nucleic acids and releases them when the electric field is reversed.

The biomolecule impermeable layer may include a layer, a membrane, or a coating that is impermeable to biomolecules, such as nucleic acids. The biomolecule impermeable layer is permeable to ions or smaller molecules; hence the ions are able to reach electrodes without any hindrance. The layer, membrane or coating may be formed by disposing a solid, semi-solid or liquid material on the electrode surface. As noted, the biomolecule impermeable layer may also comprise a "coating", wherein the coating may be deposited on the electrodes to prevent direct contact of biomolecules and the electrode materials to prevent oxidative damage to the nucleic acids.

In some embodiments, the biomolecule impermeable layer has pores with diameters in a scale of nanometer. The pore size may be large enough to pass ions or small particles, but not so large to allow passage of larger biomolecules such as proteins or nucleic acids. In some embodiments, the biomolecule impermeable layer is nanoporous, such as regenerated cellulose, and may comprise pores having diameters in the nanometer scale.

In some embodiments, the biomolecule impermeable layer comprises a polymer, wherein the polymer is selected from cellulose, sulfonated tetrafluoroethylene based fluoropolymer-copolymer, a regenerated cellulose or combinations thereof. In some embodiments of the device, the biomolecule impermeable layer comprises a sulfonated tetrafluoroethylene based fluoropolymer copolymer, which is commercially known as Nafion®. In one embodiment, the biomolecule impermeable layer comprises regenerated cellulose.

To determine the effect of the biomolecule impermeable layer during electroelution, the Pedot:PSS materials were used for electroelution under three different conditions, such as redox polymer (Pedot:PSS) electrode alone, redox polymer (Pedot:PSS) electrodes coated with a biomolecule impermeable layer and cross-linked redox polymer (Pedot:PSS) electrodes coated with a biomolecule impermeable layer. The nucleic acids obtained after electroelution using these three different types of electrodes were subjected to PCR amplification and the resulting data shown in FIG. 3 (image of DNA gel electrophoresis). Nafion® was used as a biomolecule impermeable layer to coat the redox electrodes.

In one example, the electroelution was achieved using the cross-linked and coated conductive redox polymer electrodes, wherein the eluted nucleic acid produces nucleic acid amplification products without inhibition, as shown in FIG. 3, lanes 7-8, 15-16 and 23-24 using 0V, 10V or 50V respectively. However, in the absence of crosslinking the polymer, PCR was inhibited at 0V, 10V and 50V respectively (lanes 3-4, 11-12, 19-20). The example of electrodes coated only the with Nafion® is not sufficient to prevent inhibition for PCR amplification at the higher voltage, such as 50 V (lanes 25-26). Both physical degradation (e.g., at 0V) and electrochemical degradation (e.g., at 10V or 50V) of the electrode materials needs to be eliminated to ensure amplification of the eluted nucleic acids using PCR. The cross-linking and coating of the electrodes may eliminate or reduce leaching of the electrode-degradation materials from the electrode during electroelution, and prevent inhibition of PCR amplification. The biomolecule impermeable layer helps in capturing the eluted nucleic acids after electroelution, wherein the nucleic acids are eluted from a biological sample loaded in the housing or loaded to a substrate which is inserted into the housing.

As noted, the electrode is made of Pedot:PSS polymer, wherein the electrode material is modified by cross-linking to reduce contamination of components of the electrode materials during electroelution of nucleic acid and the electrodes are coated with a biomolecule impermeable layer to prevent contact between the nucleic acids and redox active electrodes. The Pedot:PSS electrodes may be developed by soaking a cellulose membrane in the Pedot:PSS polymeric solution. Once the cellulose is completely saturated with Pedot: PSS, the Pedot:PSS soaked cellulose membrane becomes more conductive by soaking in an 80% EtOH/$H_2O$ mixture at 180° C. The Pedot:PSS soaked cellulose membrane is then immersed in a solution of 0.25 M magnesium sulfate to generate ionic cross-linking, which prevents leaching of the electrode-materials from the polymeric-electrodes during electroelution. Finally, the electrodes were either dip-coated in a Nafion® solution or covered with a nanoporous regenerated cellulose layer, which may prevent or reduce the binding of the biomolecules, such as DNA to the electrode-surface. The coated cross-linked electrodes are then cut into appropriate shapes to provide coverage over a large area of the substrates.

In one or more embodiments, the substrate is configured to receive a biological sample. In some embodiments, the substrate is self-supported or encased in a frame. One or more embodiments of the substrate comprise a solid phase matrix, semi-solid matrix, a filtration matrix, an isolation matrix, membranes or combinations thereof. The substrate may comprise one or more cell lysis reagents, one or more biomolecule-stabilizing reagents or combinations thereof. The structure and composition of the substrate is described in greater detail hereinafter.

In one or more embodiments, the device is structured in an arrangement of three major components, such as a first component, second component and third component. In some embodiments, the device comprises a first component comprising an inlet chamber and at least one electrode, such as an oxidizing electrode. The first component may comprise a biomolecule impermeable layer disposed on the oxidizing electrode. In some embodiments, the second component comprises an outlet chamber and at least one electrode, such as a reducing electrode. The second component may comprise a biomolecule impermeable layer disposed on the reducing electrode. The third component comprises a cartridge, which may be a cartridge comprising FTA™ paper. The first, second and third components are operationally coupled to each other, as shown in FIGS. 1 and 2.

The housing 12 may comprise one or more conduits for receiving the liquids to the chambers. The housing 12 may comprise an inlet and an outlet coupled to one or more chambers, wherein the inlet is used to receive the liquid from a liquid filled chamber and the outlet is used to drive the eluted nucleic acids followed by collecting and storing in a chamber, may be called as a collection chamber. In some embodiments, the housing 12 is a hermetically-sealed reservoir comprising at least two electrodes 14 and 20, operationally coupled to an inlet for receiving a sample, an electrolyte, a buffer or combinations thereof. The biomolecules are eluted from the substrate, wherein the substrate is configured to be in contact with a liquid, such as a buffer.

In some embodiments, the housing 12 comprises dried buffer salts, which may reconstitute to a buffer or an electrolyte suitable for electroelution on addition of water or a buffer solution during operation. In some embodiments, the housing 12 is an hermetically-sealed reservoir comprising one or more reagents, which can be reconstituted to an elution buffer. In some other embodiments, the housing 12 comprises one or more reagents, which can be reconstituted to a wash buffer. In some embodiments, the housing 12 comprises electrolytes. In some other embodiments, the electrolytes may be added to the housing during electroelution. In one or more embodiments, the housing may comprise one or more reagents including cell lysis or biomolecule stabilizing reagents.

In one embodiment, the device 10 may comprise a sample loading area or a sample-holder in the housing, wherein the sample is directly or indirectly loaded during the operation. The direct application of sample to the sample holder or sample loading area of the housing 12 may include the addition of sample through a pipette, a catheter, an injectable needle or a conduit. The indirect application of a sample may include addition of a sample to a substrate or to any other intermediate, which is being inserted into the device for electroelution. The intermediate may include a package, a component, a self-rupturing component or a carrier that releases the biological sample inside the housing.

In one or more embodiments, a substrate holder or a cartridge comprising a substrate 22 may be inserted to the device, wherein the substrate 28 is a sample laden substrate, ready to be incorporated into the device 10. In this embodiment, the sample is loaded to the substrate 28 when the substrate 28 is outside of the device, followed by inserting the substrate to the device. The cartridge 22 comprising sample laden substrate 28, which may be inserted to the device for electroelution of the biomolecules, such as nucleic acids from the sample for downstream analysis, application or storage. In some other embodiments, the cartridge 22 comprising the substrate 28 is embedded in the device and the sample may be loaded onto the substrate 28 during operation.

In some embodiments, as noted, the substrate is self-supported or encased in a frame 22, depending on the application requirement. The substrate is placed in a chamber or a substrate-holder 22. In some embodiments, the device comprises a sample collection substrate 28 in a cartridge or a holder 22. In one embodiment, the sample holder itself is a sample collection substrate 22, as shown in FIGS. 1 and 2.

One or more embodiments of the substrate 28 comprise a solid phase matrix, semi-solid matrix, a filtration matrix, an isolation matrix, a membrane, a mesh, a web or combinations thereof. The substrate 28 may be a porous or a non-porous material. In some aspects, the substrate 28 comprises a porous material, such as a filter membrane.

In one embodiment, the substrate 28 is hydrophilic in nature, which enables the substrate 28 to wet out quickly and completely. The hydrophilic substrate eliminates the need for expensive pre-wetting treatment and increases the flow rate of the fluid passing through the substrate.

In some embodiments, the substrate 28 is made of conductive material, such as a metal. In some embodiments, the substrate is non-metal. In one or more embodiments, the substrate 28 comprises a polymer. The non-limiting examples of polymer include a cellulose, a nitrocellulose, a nylon, a polyester and combinations thereof. The polymeric substrate may further comprise a polymer, selected from polydimethyl siloxane (PDMS), cyclic olefin copolymer (COC), polymethyl methacrylate (PMMA), poly carbonate (PC) or other materials with graftable surface chemistries. In one embodiment, the substrate comprises cellulose with biomolecule-stabilizing agents, cell lysis reagents or combinations of two or more of these impregnated therein.

In some embodiments, the substrate 28 is made of silica, glass or quartz. In an alternate embodiment, the substrate may be a glass-based matrix, such as glass fiber or glass wool may be used as substrate. In one embodiment, the substrate 28 is a solid phase extraction matrix made of a siliceous material. In some embodiments, the siliceous matrix is impregnated with the reagents. The substrate 28 may be a quartz-based membrane or matrix. The density of silanol groups on quartz matrix, when compared to standard silica matrix, may facilitate a faster and easier extraction of the nucleic acids from the biological materials.

As noted, in one embodiment, the device 10 comprises a solid phase extraction matrix as a substrate 28, on which the solid phase extraction method can be performed. The solid phase extraction is an extraction method that uses a solid phase and a liquid phase to isolate one or more molecules of the same type, or different types, from a material. The solid phase extraction matrix is usually used to purify a sample, in some examples, before using the sample in a chromatographic or other analytical method. The general procedure is to load a material onto the solid phase extraction matrix, wash away undesired components, and then elute the desired molecules with an appropriate solvent.

In some examples, when a biological sample is loaded on to the substrate 28, wherein the cell lysis is required for isolating nucleic acids from the cells before elution, the substrate comprising cell lysis reagents may be desired. One or more cell lysis reagents, one or more biomolecule-stabilizing reagents or combinations thereof may be impregnated into the substrate 28. In some embodiments, the reagents are impregnated in the substrate in a dried, semi-dried or wet form. In one or more embodiments, the dried reagents are hydrated with buffer or a sample during elution. For example, the FTA™ substrate comprises lysis reagents in the dried form and is hydrated by the sample or buffer to reconstitute the reagents before or during elution of the biomolecules. The reagents may be added to the substrate along with the sample, before or after adding the sample.

Before elution of the nucleic acids, the biological sample may be subjected to cell-lysis. The substrate may comprise reagents, which include detergent, chaotropic agent, weak base, anionic surfactant, chelating agent, uric acid, protein denaturants, buffer or combinations thereof. The detergent may include sodium dodecylsulphate (SDS), ethyl trimethyl ammonium bromide, TritonX-100, NP-40, Brij 35 or digitonin. In one or more embodiments, the chaotrope may include potassium iodide (KI), guanidinium hydrochloride, guanidinium thiocyanate or urea. In one embodiment, the lysis reagents used herein is FTA™ lysis reagent, interchangeably used herein as FTA™ reagents. The FTA™ reagents may comprise Tris, EDTA and SDS. In a typical procedure, the cells are spotted onto the matrix, SDS lyses the cells and EDTA stabilizes the nucleic acids. Before elution of the nucleic acids, the substrate may be washed with Tris-EDTA (TE) buffer solution to remove SDS and with phenol/isopropanol to remove impurities. Such FTA™ reagents comprising 50 µl of 2% SDS, 10 mM EDTA, 60 mM Tris solution are used for cell lysis and nucleic acid purification, as described in U.S. Pat. No. 5,496,562 entitled "Solid Medium and Method for DNA Storage".

Figure 4A:
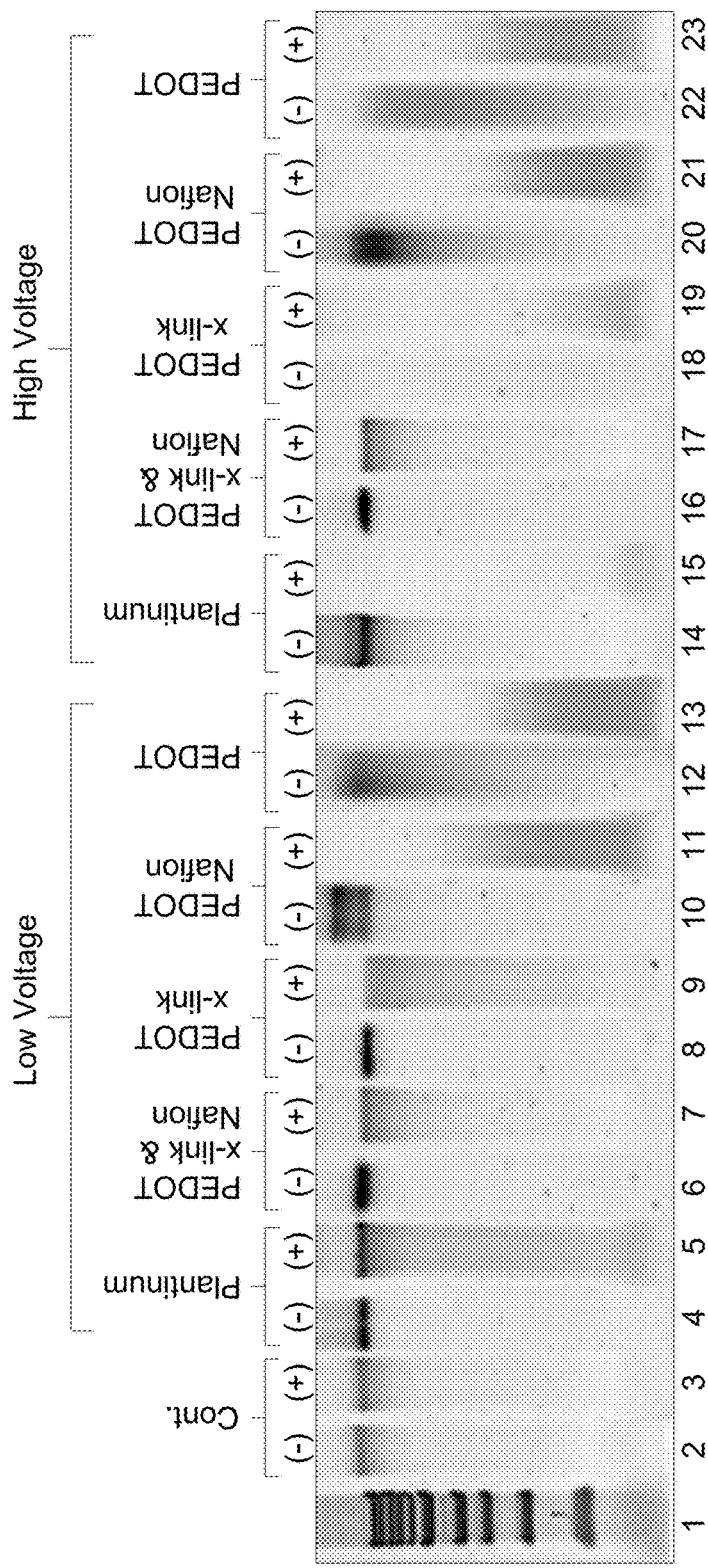

Typically, nucleic acids are bound to a solid phase extraction matrix by a salt bridge, hydrogen bonding, ionic interaction or physical entanglement. The nucleic acids are physically entangled to a cellulose-based matrix, for example, to the FTA®-cellulose membrane, wherein the nucleic acids are released from FTA®-cellulose by electroelution. In some embodiments, the nucleic acids bind to the glass or quartz-based matrices using salt bridge or hydrogen bonding interactions, whereby, the nucleic acid detachment from those matrices is much easier when compared to some other matrices, which have stronger interaction with the nucleic acids. The easy release of nucleic acids from the substrate using electroelution helps to avoid a harsh treatment on the nucleic acids, such as heating the matrices at high temperatures to elute nucleic acids, which would otherwise increase the degradation of the nucleic acids. The electroelution using cross-linked and Nafion® coated redox polymer electrodes 14 and 20 results in eluting nucleic acids without damage, as shown in FIG. 4A.

Figure 4B:
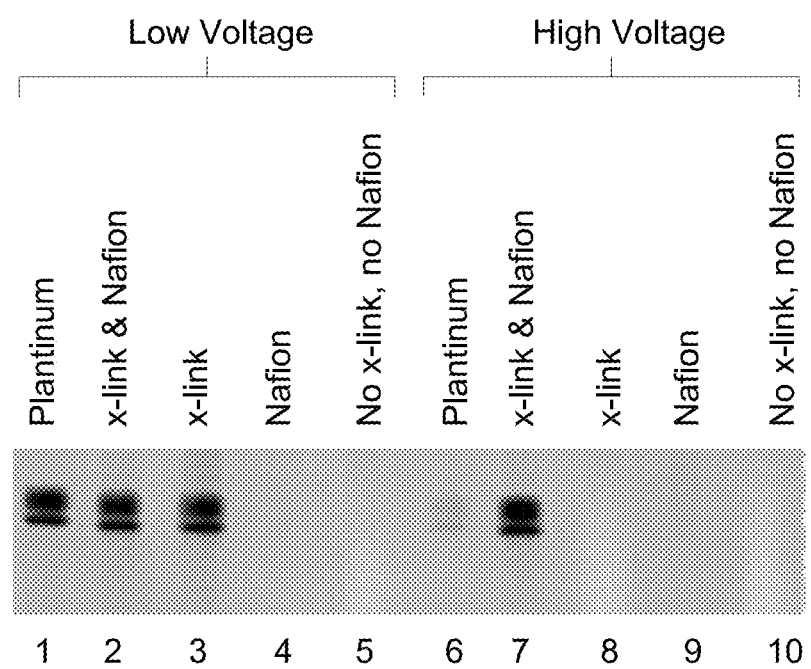

To determine oxidative damage of the DNA in contact with the electrode materials, human genomic DNA was exposed to the modified redox electrodes at 25 V (low voltage) or 210 V (high voltage) for 1 minute. The exposed DNA samples were treated with DNA repair enzyme Endonuclease IV (Endo IV) and loaded on to a 1% Agarose gel. DNA samples un-treated with the Endo IV were also loaded to the gel as a control. In case of DNA sample not treated with Endo IV, the DNA backbone remains intact and the size of the DNA also remains same. The DNA treated with Endo IV, which forms a nick at the location of the damaged bases, the DNA migration pattern changes when analyzed by denaturing gel electrophoresis. Differences in migration of the DNA incubated without Endo IV (−) and with Endo IV (+) samples indicates oxidative damage to nucleotide bases. The DNA samples were recovered from various conditions, such as using platinum electrodes, Pedot:PSS electrodes, only cross-linked Pedot:PSS electrodes, only Nafion® coated Pedot:PSS electrodes, and both cross-linked, Nafion® coated Pedot:PSS electrodes with exposure to low (25V) and high (210V) voltages. The DNA recovered after high voltage exposure were damaged and degraded, except for the sample exposed in presence of cross-linked and Nafion® coated Pedot:PSS electrodes. FIG. 4A shows that both Nafion® coating and cross-linking of PEDOT:PSS showed the reduced oxidative damage to DNA and degradation among the samples following exposure to both low and high voltages, as indicated by the lower abundance of species migrating at lower molecular weight (MW) than the samples eluted under other conditions, such as with Pedot electrodes with only cross-linking or Pedot electrodes coated with Nafion® or Platinum electrode. The electroelution of DNA under the condition of both Nafion® coating and cross-linking of PEDOT:PSS results in reduced oxidative damage to the DNA, as shown intact bands in lanes 6-7 and 16-17 of FIG. 4 A both at low voltage (25 V) exposure as well as high voltage (210 V) exposure respectively. FIG. 4B shows DNA gel with amplified product of the same DNA samples recovered from the above experiment (FIG. 4A).

As noted, the substrate may comprise an elution buffer reagent, or an elution buffer is loaded into the housing 12 during electroelution to elute the nucleic acids. The elution buffer or elution buffer reagents impregnated in the matrix 22 may comprise TE buffer. In one embodiment, 1×TE (Tris-EDTA) buffer with 0.1% Tween is dried on cellulose paper or constitutes an elution buffer solution. Elution of the nucleic acids in TE buffer is helpful if the EDTA does not affect the downstream applications. EDTA chelates divalent ions, such as magnesium, which may be present in the purified nucleic acids. The EDTA inhibits contaminating nuclease activity, as the divalent cations function as a cofactor for many of the nucleases under certain conditions.

In one or more embodiments, the elution buffer reagent is present in the housing 12 or substrate 28 in a dried, semi-dried or wet form. In some embodiments, the elution buffer reagents are hydrated by a buffer or any solvent, wherein the reagents are present in the dried form. In some embodiments, the reagents are rehydrated before eluting the nucleic acids from the substrate. The hydration is also carried out when the reagents are in a semi-dried condition. After hydration, the reagents are reconstituted in an elution buffer during electro elution of the nucleic acids.

In some embodiments, the device 10 further comprises one or more valves. At least one of the valves is operationally coupled to the housing-inlet 16, housing-outlet 18 and both. In these embodiments, the flow of liquid or elution buffer to the housing 12 is controlled by one or more valves 23 and 25, attached to the inlet or outlet (FIG. 1). The washing liquid or elution buffer may also be introduced to the device and may be controlled using the valves 23, 25. In some embodiments, the valve itself functions as a controller, while controlling the fluid flow.

In one or more embodiments, the device 10 comprises one or more controllers 30 (FIG. 1). In one embodiment, the controller is computer enabled and controls the pressure operation, fluid flow rate, fluid pressure, valve actuation, temperature of the device or combination thereof. In one or more embodiments, the controller may be a microcontroller. The controller 30 may control the actuation of the valves that regulate the fluid flow, including flow of wash buffer or elution buffer through the device to isolate nucleic acids from the biological materials. In one example, the controller 30 regulates the operation of the valves. In one or more embodiments, the device 10 may comprise a control circuit to maintain a constant current or voltage for running the device during the operation of the device. As noted, in one embodiment, the controller 30 for fluid flow may contain a check valve. In one embodiment, a controller 30 may control the initiation of connecting the circuit to start electron-ion transfer or termination of the electron-ion transfer to terminate the electroelution process. In one embodiment, the controller 30 controls the overall device to operate, wherein the controller is a switch for operating the device when the device is automated. The controller 30 may be pre-programmed before the operation depending on the application requirement or user requirement. In one example, the controller 30 comprises a micro controller circuit. In some embodiments, the controller 30 is a digital controller.

In some embodiments, the device 10 is further operatively coupled to at least one external reservoir comprising one or more fluids. In one embodiment, the working solution or electrolyte or elution buffer is stored in the external reservoir. In one embodiment, the fluid stored in the external reservoir may be a buffer, water or other solvent. In some embodiments, the fluid has a pH from about 3.5 to 8.5. In an alternative embodiment, the solution is a buffer with a pH of about 7.4 to 9.2 and an ionic strength between about 25 to about 250 mM.

In one or more embodiments, the device 10 is configured to allow collection of un-wanted materials including biological waste during the electroelution to a container. In some embodiments, the device is configured to allow collection of biomolecules of interest, such as nucleic acids to a container after electroelution from a sample. The container may be a chamber, vessel, bag or disposable. In addition, the container may be altered for easy removal of the collected biological waste or nucleic acids of interest, or the container may be integrated with an analytical device for down-stream analytical processes. The container may be coupled to the device directly or indirectly, using one or more conduits. The biological waste may contain tissue fragments, cell debris, lipids, excess reagents or other impurities.

In some embodiments, the biological sample comprises biomolecules, wherein the biomolecules comprise polysaccharides, monosaccharides, lipids, proteins, peptides, nucleic acids, metabolites, hormones and combinations thereof. In one embodiment, the biomolecules are nucleic acids. In one or more embodiments, the nucleic acids isolated from biological material include deoxyribonucleic acids (DNAs) or ribonucleic acids (RNAs). In one embodiment, the nucleic acid is deoxyribonucleic acids (DNAs). The DNA may be a genomic DNA, chromosomal DNA, bacterial DNA, plasmid DNA, plant DNA, synthetic DNA, a recombinant DNA, an amplified DNA and combinations thereof.

As noted, the isolation of nucleic acids from biological material is carried out using the device by electroelution, the biological materials used in the embodiments may comprise a physiological body fluid, a pathological body fluid, a cell extract, a tissue sample, a cell suspension, a liquid comprising nucleic acids, a forensic sample and combinations thereof. In some embodiments, the biological material is a physiological body fluid or a pathological body fluid, such as the fluid generated from secretions, excretions, exudates, and transudates, or cell suspensions such as, blood, lymph, synovial fluid, semen, saliva containing buccal swab or sputum, skin scrapings or hair root cells, cell extracts or cell suspensions of humans or animals. In some embodiments, the physiological/pathological liquids or cell suspensions may be extracted from plants. In one or more embodiments, the extracts or suspensions of parasites, bacteria, fungi, plasmids, or viruses, human or animal body tissues such as bone, liver or kidney. The biological material may also include a liquid comprising DNA, RNA and combinations thereof, mixtures of chemically or biochemically synthesized DNA or RNA.

The device 10 may be a portable or field-able device, so that the biological materials can be collected at any location and loaded into the device to isolate nucleic acids for faster downstream analysis. In some examples, the electroelution devices may run on small batteries, and thus may be used as hand held devices. In one embodiment, the electroelution device is packaged with a power source, wherein the entire assembly may be self-contained. In such embodiments, the device is portable, simplified, and user friendly.

The applications for electroelution device 10 include, but are not limited to, lab-on-a-chip devices and applications, forensics, drug delivery, liquid drug delivery, biochemical analysis, genomics, proteomics, healthcare related applications, defense and public safety applications; medical applications, pharmaceutical or biotech research applications, environmental monitoring, in vitro diagnostic and point-of-care applications, or medical devices. Other downstream applications include, but are not limited to, DNA amplification, DNA purification, PCR or real time PCR on a chip, or adaptive microfluidic mirror arrays.

In one or more embodiments, the device 10 is fully automated or partially automated. The automation of the device is required to reduce the human intervention during extraction and purification of the nucleic acids. The use of an automated device further helps in minimizing the contamination during nucleic acid purification from various biological samples. Fully automatic devices are desirable for forensic applications, wherein the objective is to purify nucleic acids from a trace amount of sample. An externally located controller may be operationally coupled to the device to drive the system, excluding any manual intervention after application of the biological sample to the device or sample inlet.

In some embodiments, the device is configured to integrate with a system, more specifically with an analytical system. As noted, the device may have one or more coupling means through which the device may integrate with another system depending on the requirement. The coupling means may include but is not limited to, an adapter, or a connector. One or more adapters may be used to couple the device with another system. In one embodiment, the adapter has a holder to hold the device and a connector for connecting to the system. In some other embodiments, an adapter may be coupled to the device, wherein the adapter has at least two holders for holding the device and the system on it, and thereby couple the device with the system. For example, an adapter is used for coupling the device with a downstream analytical system. In some embodiments, the device itself is configured to have one or more holders, connecting ports or combination thereof, which mechanically couples the device to another system. The device may be electronically coupled to another system for downstream applications.

As noted, the device is configured to integrate with a system, the system may be a microfluidic system or a conventional analytical system. In one embodiment, the device is coupled to a downstream microfluidic system. By translating and miniaturizing the device, the need for manual intervention between different steps is eliminated. Microfluidic technology provides a high-speed, high-throughput nucleic acid sample preparation process. As the dimension of the device is in micrometer or in millimeter scale, the device is compatible to integrate with any system, especially with microfluidic attachments, such as a micrometer or millimeter scale fluidic system. The electroelution device is disposed into a channel, wherein the channel may be a microfluidic channel.

One or more embodiments of a system, comprises an inlet port for receiving sample, reagents, buffers or combinations thereof and an outlet port for recovering a sample after electroelution, one or more reservoirs configured to contain a buffer, a solvent, a reagent or combinations thereof, an electroelution device, and a controller. In some embodiments, the controller is a processor-enabled controller. In some other embodiments, a system comprises a port for receiving biological sample, reagents, buffers or electrolytes; an electroelution device; a port for priming the device with a buffer or solvent; and a controller. As noted previously, the device used herein comprises a substrate; biomolecule impermeable membrane disposed on the electrodes, wherein the substrate and housing are operationally coupled to each other. The outlet port for recovering a sample after electroelution may be coupled to a collection chamber to collect eluted nucleic acids.

As illustrated by FIG. 8, one embodiments of a system is depicted, wherein the system 32 comprises an electroelution device 10. The system comprises an inlet port 36 for receiving sample on the substrate. The system further comprises another inlet port 34 for receiving reagents, buffers or combinations thereof. One or more reservoirs 38 configured to contain a buffer, a solvent, a reagent or combination of these, wherein the reservoir is included to the system 32. In one embodiment, the reservoir 38 is coupled to the device 10 through a conduit 40 and it opens to the system. The system further comprises a controller 42, which is a processor-enabled controller. The system further comprises an outlet port 44 for recovering a sample after electroelution and a reservoir 46 collects the sample after electroelution.

In some embodiments, the system is further integrated with one or more additional devices. As noted, the system is further integrated with one or more additional devices for various downstream applications, such as nucleic acid analysis, nucleic acid sequencing, nucleic acid amplification, disease detection and combinations thereof. The additional device may include, but are not limited to, a nucleic acid amplification device, such as a polymerase chain reaction (PCR) machine, a nucleic acid analyzer, or a nucleic acid sequencing machine.

In one or more embodiments, the system further comprises one or more containers for collecting nucleic acids or washing liquid devoid of biomolecule of interest. In one or more embodiments, the non-limiting examples of containers are bag, chamber and vessels. The containers may be disposable or reusable. Various components of the device may be operationally connected to each other using conduits, holder, adapter, or valves. The system may further comprise one or more sensors, such as temperature sensor, pressure sensor, flow sensor or pH sensor.

EXAMPLE 1

Inhibition of Bioassays Using Conductive Monomeric or Polymeric Electrode Materials Materials: The substrates including 31-ETF cellulose (GE-Whatman, UK), FTA™ card (from GE Healthcare) were used for sample loading followed by electroelution. Illustra PuRe Taq Ready-to-Go™ PCR beads (from GE Healthcare) were used for DNA amplification using PCR.

The use of standard conductive electrode materials, such as conductive monomers or polymers for electroelution of the biomolecules may have effect on downstream biological applications. The effect of standard conductive monomers or polymers including PSS monomers, PSS polymers and Pedot: PSS polymers on amplification of nucleic acids by polymerase chain reaction (PCR) was determined, data is presented in Table 1.

The conductive polymer electrode materials were added to the PCR mixtures, which were run in an ABI 7500 PCR machine using SYBR© Green reagents and standard curve quantification. The electrode base materials including PSS monomers, PSS polymers and Pedot: PSS polymers were added to the PCR mixture at different concentrations, as shown in the left column of Table 1. Reactions were run in triplicate using primers for the vWA CODIS loci. Successful amplifications are denoted with a "+", successful but delayed (higher than expected $C_t$ value) amplifications are denoted with "+/-", while completely inhibited reactions are denoted with a "−". The threshold of inhibition was measured at $6.5 \times 10^{-5}$ PPM for Pedot:PSS and PSS polymer, and at 0.65 PPM for the PSS monomer.

TABLE 1

Inhibition of nucleic acid amplification: use of different monomers and polymers.

| PPM | Pedot: PSS | PSS MW70 | PSS Monomer |
|---|---|---|---|
| 650 | − | − | − |
| 65 | − | − | − |
| 6.5 | − | − | − |
| 0.65 | − | − | +/− |
| 0.065 | − | − | + |
| $6.5 \times 10^{-3}$ | − | − | + |
| $6.5 \times 10^{-4}$ | − | − | + |
| $6.5 \times 10^{-5}$ | +/− | +/− | + |
| $6.5 \times 10^{-6}$ | + | + | + |
| $6.5 \times 10^{-7}$ | + | + | + |

As presented in Table 1, the standard electrode base materials showed the inhibitory effect on nucleic acid amplification. Pedot:PSS polymer and PSS of molecular weight 70 kD inhibit the amplification reactions at a very low concentration of $6.5 \times 10^{-5}$ ppm. However, the PSS monomer has little effect on PCR amplification as the assay shows positive results for most concentrations used. Therefore, Pedot:PSS conductive polymer inhibits the PCR reaction even when present at a lower concentration, such as $6.5 \times 10^{-5}$ ppm. The discharge of trace amount of electrode materials during electroelution may also cause detrimental effects on nucleic acids and the downstream applications, such as amplification of the nucleic acids.

EXAMPLE 2

Cross-linking and Coating of Electrodes Reduce Bioassay-inhibition

DNA was eluted from a biological sample using the device (FIG. 1). The eluted DNA was collected and exposed to an electric field, followed by testing for bioassay-inhibition. The PCR amplification reaction was effected with the eluted DNA using the device comprising different forms of Pedot:PSS electrodes. In the first set, the device contained Pedot: PSS electrodes without any cross-linking or coating, in the second set, the device contained Pedot: PSS electrodes modified with ionic-cross linking, in the third set, the device contained Pedot:PSS electrodes with ionic cross-linking and coated with Nafion® (PLBC02510), and in the fourth set, the device contained Pedot: PSS electrodes coated with Nafion®. In each of the cases, the DNA was eluted using different voltages.

The eluted DNA was washed without applying any voltage such as 0 V for 100 mins, and in other cases the eluted DNA was exposed to 10 V and 50 V for 5 minutes of continuous operation of direct current (DC) with 4 mm electrode spacing.

A PCR was effected as a bioassay using buffer, dNTPs and Taq DNA polymerase with the eluted DNA as a template. PCR was performed with a 23 μL and 12.5 μL of DNA sample eluted and collected from the device. Amplification mixtures were run in Illustra™ PuReTaq Ready-To-Go PCR Beads using primers for 829 bp human genomic target. The primer sequences used for amplifications included forward primer GCAGAATGGTAGCTGGATTG (SEQ ID NO.: 1) and reverse primer CCTCAAGGGCACCTTTGCCA (SEQ ID NO.: 2). The PCR amplification included a cycling program: the first cycle at 95° C. for 10 minutes; and the next 30 cycles included sequential incubation at 95° C. for 15 seconds; 58° C. for 30 seconds and 72° C. for 1 minute. The reaction mixture after 30 cycles was further incubated at 72° C. for 10 minutes.

The amplification reaction was inhibited by the PEDOT: PSS electrode materials even without applying any voltage (during washing) when the concentration of eluate (23 μL) is high (lane 3) as shown in FIG. 3. The inhibition of amplification was even greater when the applied voltage is higher, at 10 V or 50 V for PEDOT:PSS electrode (lanes 11-12, 19-20) at both lower (12.5 μL) and higher (23 μL) concentrations.

FIG. 3 further illustrates that the DNA samples, which were eluted in the presence of cross-linked electrodes, produced amplified product under the condition of exposure at 0 V, 10 V (at low) or 50 V (high voltage) for both 12.5 μL and 23 μL samples without inhibition (lanes 5-6, 13-14 and 21-22). The cross-linked electrode materials reduced leaching of the electrode-degradation materials during electroelution, which helps in PCR amplification reactions without inhibition.

The cross-linked and Nafion® coated electrodes resulted in amplification without inhibition when washed at 0 V or when low (10 V) or high (50 V) voltages were applied. In one example, the electroelution was effected with the cross-linked and Nafion® coated conductive redox polymer electrodes, wherein the eluted nucleic acid produces nucleic acid amplification products without inhibition, as shown in FIG. 3, lanes 7-8, 15-16 and 23-24 using 0V, 10V or 50V respectively. The DNA sample eluted in the presence of only the cross-linked electrodes, and the electrodes both cross-linked and Nafion® coated are enabled amplification at high voltage (50V) without inhibition.

The DNA samples, eluted using electrodes coated with only Nafion®, were not sufficient to prevent inhibition of PCR amplification at the higher applied voltage, such as 50 V (lanes 25-26) compared to at no applied voltage (0 V) or at a lower applied voltage (10 V) where the PCR amplification is not inhibited (as shown in lanes 9-10, and 17-18 respectively).

EXAMPLE 3

Use of Conductive Redox Polymer Electrodes: Recovery of Non-damaged DNA

One μg of human genomic DNA in solution was placed in a disposable cuvette and exposed to electric field for 1 minute at low (25 volts) or high (210 volts) voltages in presence of different types of electrodes, Platinum, Pedot, cross-linked Pedot, Nafion® coated Pedot or cross-linked and Nafion® coated Pedot. DNA was quantified using fluorometric DNA intercalating dye assay. To determine oxidative damage of DNA in contact with the electrode materials DNA samples were treated with DNA repair enzymes 8-oxoguanine DNA Glycosylase and Endonuclease IV. DNA samples were further loaded on to a 1% Agarose gel for visualization. In FIG. 4, the results are illustrated, wherein the samples which were not treated with Endo IV are indicated by (−) and those were treated with Endo IV are indicated by (+). The Endo IV treatment is also referred to herein as a "nicking assay" or "DNA damage assay". The assay is based on identifying damaged bases of the DNA molecules and repaired by Endo IV. In the case of DNA treated with DNA repaired enzyme Endo IV, the enzyme forms a nick in the location of the damage bases as the damage base is removed, results in nicking of the DNA backbone, which results in change in DNA migration pattern as visualized by denaturing gel electrophoresis. In the case of DNA samples not treated with Endo IV, the DNA backbone remains intact and gel-migration pattern of the DNA also remains same.

The same DNA was then amplified using Illustra™ PuReTaq Ready-To-Go PCR Beads. The PCR amplification was effected as a bioassay using buffer, dNTPs and Taq DNA polymerase with the treated DNA as a template. Amplification mixtures were run in Illustra™ PuReTaq Ready-To-Go PCR Beads using primers for the vWA CODIS loci. The primer sequences used for amplifications included forward primer AATAATCAGTATGTGACTTGGATTGA (SEQ ID NO.: 3) and reverse primer ATAGGATGGATGGATA-GATGGA (SEQ ID NO.: 4). The PCR amplification included cycling program: first cycle at 95° C. for 10 minutes; and next 30 cycles included sequential incubation at 95° C. for 15 seconds; 58° C. for 30 seconds and 72° C. for 1 minute. The reaction mixture after 30 cycles was further incubated at 72° C. for 10 minutes.

The gel electrophoresis image includes samples recovered after the DNA damage or nicking assay, as shown in FIG. 4 A. The Nafion® coated and cross-linked PEDOT electrode showed the highest quality DNA at the higher applied voltage (lane 17, at 210 V) compared to inert platinum electrode (lane 15), cross-linked electrode (lane 19), Nafion® coated electrode (lane 21) and un-modified Pedot electrode (lane 23). Even the "inert" platinum electrode caused significant DNA damage at this high voltage, as observed by presence of lower molecular weight single stranded DNA as visualized by denaturing gel electrophoresis (lane 15). The redox polymer electrode or redox polymer electrode with a single treatment (cross-link or coating) is not sufficient to prevent the DNA-damage as shown in FIG. 4 (lanes 19, 21 and 23). The DNA samples, exposed to high voltage (210 V) in presence of cross-linked and Nafion® coated redox electrode, enabled amplification of the DNA (lane 8), as shown in FIG. 4 B. Under a lower applied voltage (25 V), less degradation was observed in the platinum electrode, cross-linked and Nafion® coated Pedot electrode and cross-linked Pedot electrode (lanes 2, 3, and 4, respectively).

EXAMPLE 4

Efficient Elution of DNA Under Different Conditions

To confirm efficient elution of the DNA sample using the device of the present invention, lambda DNA was used and eluted under different applied voltages. In two different sets, 45 V and 5 V were applied across a cellulose matrix comprising 1 μg of lambda DNA, which was applied to the cellulose matrix prior to the device assembly. The device was loaded with elution buffer, and voltage was applied for five minutes to capture DNA on the Nafion® coated electrodes. The electric field was then reversed to repel DNA from the Nafion® coated electrode surface and back into solution, and finally the elution buffer was collected from the device at 100 μL/min flow rate. The yield of the applied lambda DNA was calculated using fluorometric DNA intercalating dye assay. The ability to capture DNA more quickly using the higher electric fields (45 V) was compared to lower electric fields (5 V), as shown in FIG. 5 as a graph of the elution profile of the lambda DNA from the device using different applied voltages.

In another example, electroelution was performed with 1 μg of lambda DNA, which was applied to the cellulose substrate and allowed to dry. The experiment was carried out in two sets, in one set, 25 volts were applied to the DNA sample for five minutes to elute the DNA and captured on the Nafion® coated electrode surface, and in the second set, no electric field was applied to the DNA sample to capture the DNA on the Nafion® coated electrode surface. The collected DNA was eluted at 100 μL/min flow rate from the device and the yield was calculated using fluorometric DNA intercalating dye assay. The results shown in FIG. 6 illustrate a much higher amount of eluted DNA using active elution under an applied electric field of 25 V when compared to passive elution wherein no electric field was applied.

In another experiment, the electroelution was achieved directly from a paper punch obtained from a GE/Whatman Easicollect™ buccal sample collector. For electroelution, 25 volts were applied for 5 minutes and the eluate was collected at a flow rate of 100 μL/min Data represents in FIG. 7 for three individual runs where the error bars indicate standard deviation. FIG. 7 demonstrates the applicability of the device for rapid elution of DNA under 25 V for 5 minutes, wherein the sample was collected using a commercially available bio-sample collection device.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method of eluting biomolecules from a biological sample, comprising:
   loading the biological sample to a device comprising a housing, at least two conductive redox polymer electrodes operationally coupled to the housing and a biomolecule impermeable layer disposed on at least one of the electrodes;
   initiating an electrical connection to generate an electric field strength sufficient to elute biomolecules from the biological sample, wherein the electric field strength is at least about 400 V/cm; and
   eluting the biomolecules from the biological sample, wherein eluting the biomolecules comprises electrophoretically eluting the biomolecules from the biological sample, wherein the at least two conductive redox polymer electrodes comprise conductive redox polymers of 0.05 µg-0.5 mg per $mm^2$ of electrode surface and the conductive redox polymer is cross-linked.

2. The method of claim 1, wherein the conductive redox polymer is selected from polyacetylenes, polyphenylene vinylenes, polypyrroles, polyThiophenes, polyanilines, polyphenylene sulfide, or polyfluorenes.

3. The method of claim 1, wherein the conductive redox polymer comprises cross-linked Pedot-PSS and the biomolecule impermeable layer comprises a sulfonated tetrafluoroethylene based fluoropolymer-copolymer.

4. The method of claim 1, wherein the loading of the biological sample is effected by direct loading of the biological sample to the housing, loading of a biological sample laden substrate into the housing, loading of the biological sample in a package configured to release the sample during operation, or combinations thereof.

5. The method of claim 1, further comprising wetting the electrodes and the biomolecule impermeable layer.

6. The method of claim 1, further comprising electrophoretically driving the eluted biomolecules to a surface of the biomolecule impermeable layer.

7. The method of claim 1, further comprising releasing the biomolecules from the surface of the biomolecule impermeable layer by reversing an ion-conduction between the electrodes.

8. The method of claim 7, further comprising eluting impurities from the housing.

9. The method of claim 1, wherein the conductive redox polymer comprises Pedot-PSS.

10. The method of claim 1, wherein the housing comprises a cylindrical cartridge, a microfluidic channel or combinations thereof.

11. The method of claim 1, wherein the biomolecule impermeable layer comprises cellulose, sulfonated tetrafluoroethylene based fluoropolymer-copolymer or combinations thereof.

12. The method of claim 1, wherein the biomolecules are nucleic acids.

13. The method of claim 1, wherein the biological sample comprises a blood, a buccal swab, a body fluid, a serum, a sputum, an excretory product, a cell-extract, a cell, a tissue, a liquid comprising nucleic acids or combinations thereof.

14. The method of claim 1, further comprising wetting the electrodes by adding an electrolyte to the housing.

15. A method of eluting nucleic acids from a biological sample, comprising:
   loading the biological sample to a device comprising a housing, at least two conductive redox polymer electrodes operationally coupled to the housing and a biomolecule impermeable layer disposed on at least one of the electrodes;
   initiating an electrical connection to generate an electric field strength sufficient to elute nucleic acids from the biological sample, wherein the electric field strength is at least about 25 V/cm; and
   eluting the nucleic acids from the biological sample, wherein eluting the nucleic acids comprises electrophoretically eluting the nucleic acids from the biological sample, wherein the at least two conductive redox polymer electrodes comprise conductive redox polymers of 0.05µg-0.5 mg per $mm^2$ of electrode surface and the conductive redox polymer is cross-linked.

16. The method of claim 15, wherein the conductive redox polymer comprises cross-linked Pedot-PSS and the biomolecule impermeable layer comprises a sulfonated tetrafluoroethylene based fluoropolymer-copolymer.

17. The method of claim 15. further comprising wetting the electrodes and the biomolecule impermeable layer.

18. The method of claim 15, further comprising electrophoretically driving the eluted biomolecules to a surface of the biomolecule impermeable layer.

19. The method of claim 15, further comprising releasing the biomolecules from the surface of the biomolecule impermeable layer by reversing an ion-conduction between the electrodes.

20. The method of claim 19, further comprising eluting impurities from the housing.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcagaatggt agctggattg                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctcaagggc acctttgcca                                                    20

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aataatcagt atgtgacttg gattga                                             26

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ataggatgga tggatagatg ga                                                 22
```